United States Patent [19]

McRae

[11] Patent Number: Plant 6,324

[45] Date of Patent: Oct. 4, 1988

[54] LILY PLANT NAMED 'COLLEEN'

[75] Inventor: Edward A. McRae, Boring, Oreg.

[73] Assignee: Melridge Inc., Aurora, Oreg.

[21] Appl. No.: 923,061

[22] Filed: Oct. 24, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new variety of hybrid lily plant particularly characterized by the starry form of its flowers of light cream to white coloring having very delicate spotting, the flowers appearing in large clusters and being of excellent form and long persistence both on the plant and as cut flowers. This plant is highly resistant to disease and shows high tolerance of virus, making it an excellent garden plant and being particularly suited to forcing and to mass commercial cultivation. The bulbs of this plant may be precooled and forced for cut flower production and the clone is vigorous and is a good grower and propagator.

1 Drawing Sheet

BACKGROUND OF THE INVENTION

This new variety of lily plant originated as a seedling selected by me from a group of seedlings resulting from my crossing the clonal cultivar 'Sterling Star' and the clonal cultivar 'Connecticut King' as the pollen parent, with the object of producing lilies in cream and white color tones well suited for forcing for cut flower production out of season, heretofore unknown in the lily breeding art. This particular seedling was selected for propagation because of the large size and starry form of its flowers, which are borne in an upright orientation and have the soft cream to white color which I sought, the color pattern being accented by its delicate spotting and the flowers being produced as a raceme on a single stalk. This selected seedling was reproduced by me and under my direction at Sandy, Oreg., and successive generations produced by bulb scale propagation, and by natural propagation from bulblets, have demonstrated that the novel and distinctive characteristics of this new lily variety are fixed and hold true under asexual propagation from generation to generation.

Work with this new lily variety has demonstrated its excellent character for forcing out of season when the bulbs are dug at the appropriate time and properly precooled; October-dug bulbs, properly precooled and potted in January, will flower under glass in western Oregon with no supplementary lighting and at moderate greenhouse temperatures in an average of about 75 to 85 days.

DESCRIPTION OF THE DRAWING

My new lily plant variety is illustrated by the accompanying photographic drawing, which in the upper view shows a group of stems, buds and open flowers, and in the lower view shows a face view of a fully opened flower illustrating the flower form, the tepal arrangement, and the distinctive lightly spotted pale cream to white flowers.

DESCRIPTION OF THE NEW VARIETY

The following is a detailed description of my new variety of Asiatic hybrid lily, with nomenclature according to The International Lily Register (The Royal Horticultural Society of London, Second Edition, 1969), and with the color designations according to The R.H.S. Colour Chart published by The Royal Horticultural Society in 1966.

THE PLANT

Origin: Seedling.

Parentage:

*Seed parent.*—Lilium 'Sterling Star' (unpatented).

*Pollen parent.*—Lilium 'Connecticut King' (unpatented).

Classification:

*Horticultural.*—Upright Asiatic Hybrid Lily, Division I-A, according to the Horticultural Classification of Lilies by The Royal Horticultural Society of London.

*Commercial.*—Hybrid Lilium Clone.

Form: Single stem, erect and stately.

Height: About 75 to 85 cm. stem produced by glasshouse forcing of bulbs of a size of about 15 to 18 cm. in circumference. Bulbs in their second year of growth after scale propagation in the field produce stems averaging about 100 cm. in height.

Growth: Vigorous and upright.

Foliage:

*Quantity.*—Abundant.

*Leaf size.*—About 7 to 10 cm. long and about 1 to 2 cm. wide.

*Leaf shape.*—Lanceolate with acuminate tip.

*Texture.*—Leathery.

*Aspect.*—Glossy, and lightly pubescent along the margins.

*Color.*—Medium green, lighter on the under side.

Bulbs:

*Size.*—Various, ranging up to 25 cm. in circumference in commercial use.

*Color.*—White.

THE BUD

Form: Long ovoid and obtuse.

Size: About 8 to 9 cm. long and about 5 cm. in circumference just prior to opening.

Opening rate: The bud opens slowly, in response to morning light, in about one hour.

Color: Palest cream to white just prior to opening and as the tepals unfurl.

Peduncle:

*Length.*—Averages about 4to 6 cm., but may elongate if light levels are too low or if bulbs have been improperly stored prior to forcing.

*Color.*—Medium green with light plum overlay.

THE FLOWER

Blooming habit: Annually, once and profusely in mid-season.

Size: Large, averaging about 14 to 17 cm. in diameter.

Borne: On a single stem as a raceme, producing about 8 to 12 buds from a bulb about 12 to 15 cm. in circumference.

Shape: Cup-shaped when bloom first opens, becoming flattened as the tepals recurve during the second day.

Tepalage:

*Number.*—Six.

*Arrangement.*—Hexagonal and slightly imbricated.

*Shape.*—Long ovate with entire margins and acute tips.

*Appearance.*—Shiny.

*Color.*—The overall color is an extremely pale cream, RHS 9D, when the flowers first open, fading to substantially pure white by the second day. The border of the nectary furrow is slightly pubescent and white.

*Tepal spotting.*—The basal third of each tepal is marked with many small magenta-purple spots at each side of the nectary furrow.

*Color changes.*—As the flower ages, the color fades to a pure white, if the light levels are adequate for cut-flower maintenance.

Pedicel:

*Length.*—About 5 to 15 cm., in average.

*Form.*—Sturdy and ascending upwardly at about 45° from the horizontal. Secondary buds occur very rarely.

*Color.*—Medium green.

Persistence: The tepals stay on the stem about three weeks.

Fragrance: None.

Lasting quality: The flower is long lasting both on the plant and as a cut flower.

THE REPRODUCTIVE ORGANS

Stamens:

*Number.*—Six.

*Arrangement.*—Typical of the genus Lilium.

*Anthers (dehisced) and pollen.*—Greyed orange, 167A.

*Filaments.*—Length: About 5 cm. Color: Soft cream, 9 D.

Pistils:

*Number.*—One.

*Style.*—Length: About 5 cm.

*Stigma.*—Color: Soft green with deep plum overlay.

Character of ovary: Typical of the genus Lilium.

THE FRUIT

Fertility: The fruit is fertile.

Shape: Ovoid.

Color at maturity: Soft brown, often overlaid with soft plum.

This new lily variety closely resembles 'Sterling Star' but it has shorter stems and much better shaped flowers; and wider, thicker and more abundant leaves. This new plant is more reliable and uniform in its forcing performance and its flowers have a more starry form and are more cupped than those of 'Sterling Star', the flower color, upon first opening, being creamier at the tips and greener at the center than those of 'Sterling Star'.

I claim:

1. A new and distinctive variety of Asiatic hybrid lily, substantially as herein shown and described, characterized by its large flowers of "starry" form having a soft cream to pure white color, enriched by delicate spotting at the base portion of the tepals; its vigorous growth habit and rapid natural propagation; and its resistance to disease with high tolerance of virus.

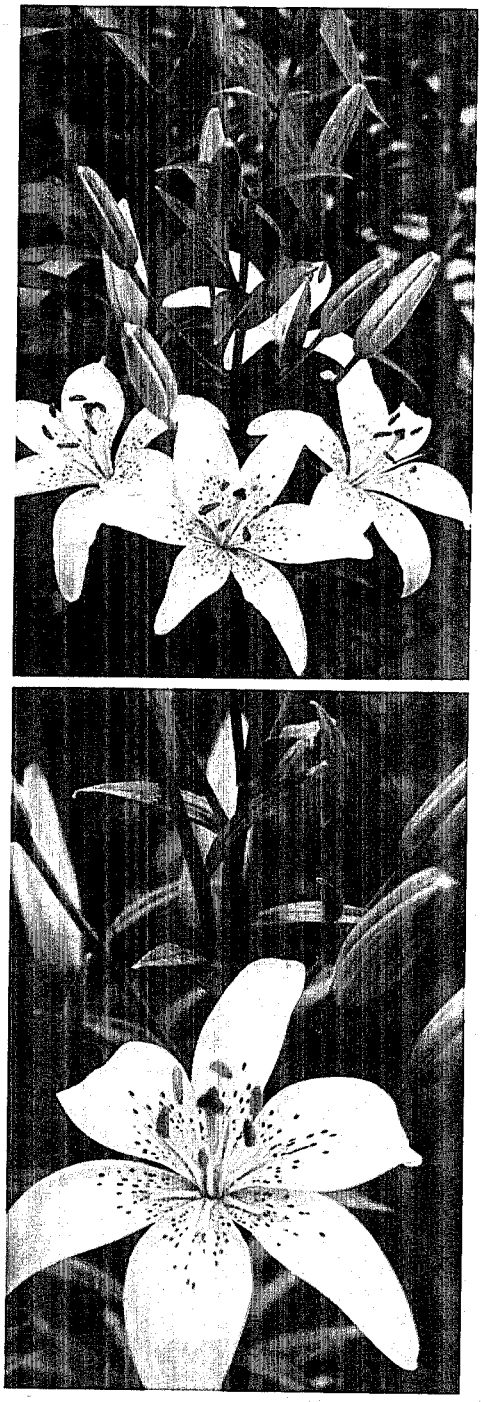

* * * * *